(12) United States Patent
Marfurt et al.

(10) Patent No.: US 9,039,878 B2
(45) Date of Patent: *May 26, 2015

(54) MEDIATOR FOR TEST SENSOR (71) Applicant: BAYER HEALTHCARE LLC, Tarrytown, NY (US)

(72) Inventors: Karen L. Marfurt, Edwardsburg, MI (US); Henry C. Arndt, Elkhart, IN (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/717,024

(22) Filed: Dec. 17, 2012

(65) Prior Publication Data

US 2013/0126350 A1 May 23, 2013

Related U.S. Application Data

(60) Continuation of application No. 13/207,855, filed on Aug. 11, 2011, now Pat. No. 8,357,797, which is a division of application No. 12/316,115, filed on Dec. 9, 2008, now Pat. No. 8,022,204.

(60) Provisional application No. 61/007,178, filed on Dec. 10, 2007.

(51) Int. Cl.
*G01N 27/327* (2006.01)
*C12Q 1/00* (2006.01)
(Continued)

(52) U.S. Cl.
CPC ............ *G01N 27/3271* (2013.01); *C12Q 1/004* (2013.01); *C07D 265/38* (2013.01); *C07D 279/18* (2013.01); *C07D 279/20* (2013.01)

(58) Field of Classification Search
CPC ............ G01N 27/327; G01N 27/3271; G01N 27/3272; G01N 27/3273; G01N 27/3274; C07D 279/18; C07D 279/20; C07D 265/38; C09B 21/00; C09B 19/00; C08F 8/44
USPC ................ 544/36, 37; 204/403.01–403.15
See application file for complete search history.

(56) References Cited

U.S. PATENT DOCUMENTS 4,125,717 A 11/1978 Psaar
4,362,873 A 12/1982 Belfort
(Continued)

FOREIGN PATENT DOCUMENTS

EP 0 117 302 A2 9/1984 ........... C07D 279/28
EP 0 177 317 A1 4/1986 ...................... 279/18
(Continued)

OTHER PUBLICATIONS

Written Opinion of the International Searching Authority corresponding to International Patent Application No. PCT/US2008/085810, European Patent Office, dated Apr. 2, 2009, 9 pages.
(Continued)

*Primary Examiner* — J. Christopher Ball
(74) *Attorney, Agent, or Firm* — Nixon Peabody LLP (57) ABSTRACT

A method of forming a 3-phenylimino-3H-phenothiazine or a 3-phenylimino-3H-phenoxazine mediator includes providing a first reactant including phenothiazine or phenoxazine, providing a first solvent, providing a second reactant and providing a second solvent. The first reactant, first solvent, second reactant and second solvent are combined to form a reactants solution. Sodium persulfate is added to the reactants solution to couple the first and second reactants resulting in a reaction solution including the 3-phenylimino-3H-phenothiazine or the 3-phenylimino-3H-phenoxazine mediator.

40 Claims, 4 Drawing Sheets

(51) Int. Cl.
*C07D 265/38* (2006.01)
*C07D 279/18* (2006.01)
*C07D 279/20* (2006.01)

(56) References Cited

U.S. PATENT DOCUMENTS

| | | |
|---|---|---|
| 4,545,382 A | 10/1985 | Higgins et al. |
| 4,702,863 A | 10/1987 | Bugaut et al. |
| 4,710,570 A | 12/1987 | Thien |
| 4,711,245 A | 12/1987 | Higgins et al. |
| 4,863,016 A | 9/1989 | Fong et al. |
| 4,941,308 A | 7/1990 | Grabenkort et al. |
| 5,120,420 A | 6/1992 | Nankai et al. |
| 5,206,147 A | 4/1993 | Hoenes |
| 5,212,092 A | 5/1993 | Jackson et al. |
| 5,236,567 A | 8/1993 | Nanba et al. |
| 5,298,144 A | 3/1994 | Spokane |
| 5,334,508 A | 8/1994 | Hoenes |
| 5,393,615 A | 2/1995 | Corey et al. |
| 5,411,647 A | 5/1995 | Johnson et al. |
| 5,498,542 A | 3/1996 | Corey et al. |
| 5,520,786 A | 5/1996 | Bloczynski et al. |
| 5,631,371 A | 5/1997 | Bloczynski |
| 5,798,031 A | 8/1998 | Charlton et al. |
| 5,801,057 A | 9/1998 | Smart et al. |
| 6,057,120 A | 5/2000 | Heindl et al. |
| 6,221,586 B1 | 4/2001 | Barton et al. |
| 6,299,757 B1 | 10/2001 | Feldman et al. |
| 6,773,564 B1 | 8/2004 | Yugawa et al. |
| 7,163,616 B2 | 1/2007 | Vreeke et al. |
| 8,022,204 B2 * | 9/2011 | Marfurt et al. .............. 544/37 |
| 8,357,797 B2 * | 1/2013 | Marfurt et al. .............. 544/36 |
| 2002/0099308 A1 * | 7/2002 | Bojan et al. .............. 600/573 |
| 2004/0185517 A1 * | 9/2004 | Marfurt .............. 435/14 |
| 2007/0080073 A1 * | 4/2007 | Wu et al. .............. 205/777.5 |
| 2009/0145775 A1 | 6/2009 | Chu et al. |

FOREIGN PATENT DOCUMENTS

| | | | |
|---|---|---|---|
| EP | 0 775 669 A1 | 5/1997 | .............. 265/38 |
| GB | 2132194 A | 7/1984 | .............. C07D 279/28 |
| GB | 2 141 437 A | 12/1984 | |
| JP | S 608249 | 1/1985 | |
| JP | S 6189260 | 5/1986 | |
| JP | 2011-505834 | 3/2011 | |
| SU | 1436874 | 11/1988 | .............. C07D 279/28 |

OTHER PUBLICATIONS

Andreani et al., "Ladder Oligophenothiazines by Direct Thionation of N-Arylanilino Derivatives;" Journal of Heterocyclic Chemistry, vol. 28, 1991, Mar. 1991, pp. 295-299 XP002516206.

* cited by examiner

MEDIATOR FOR TEST SENSOR

CROSS REFERENCE TO RELATED APPLICATION

This application is a continuation application of application Ser. No. 13/207,855, filed on Aug. 11, 2011, which has been allowed; application Ser. No. 13/207,855 is a divisional application of application Ser. No. 12/316,115 filed on Dec. 9, 2008, which issued as U.S. Pat. No. 8,022,204 on Sep. 20, 2011; application Ser. No. 12/316,115 claims priority to Provisional Application No. 61/007,178 filed on Dec. 10, 2007, which are incorporated by reference in their entireties.

FIELD OF THE INVENTION

The present invention generally relates to a method forming a mediator. More specifically, the present invention generally relates to a method of forming a mediator to be used in an electrochemical test sensor that is adapted to assist in determining information related to an analyte.

BACKGROUND OF THE INVENTION

The quantitative determination of analytes in body fluids is of great importance in the diagnoses and maintenance of certain physical conditions. For example, lactate, cholesterol and bilirubin should be monitored in certain individuals. In particular, it is important that individuals with diabetes frequently check the glucose level in their body fluids to regulate the glucose intake in their diets. The results of such tests can be used to determine what, if any, insulin or other medication needs to be administered. In one type of blood-glucose testing system, test sensors are used to test a sample of blood.

A test sensor contains biosensing or reagent material that reacts with, for example, blood glucose. One type of electrochemical test sensor is a multilayer test sensor that includes a base or substrate and a lid. Another type of electrochemical test sensor includes a base, a spacer and a lid. Existing electrochemical test sensors include at least two electrodes in the form of an electrode pattern. A potential is applied across these electrodes and a current is measured at the working electrode. The current measurement is directly proportional to the size of the working electrode.

Electrochemical test sensors are based on enzyme-catalyzed chemical reactions involving the analyte of interest. In the case of glucose monitoring, the relevant chemical reaction is the oxidation of glucose to gluconolactone or its corresponding acid. This oxidation is catalyzed by a variety of enzymes, some of which may use coenzymes such as nicotinamide adenine dinucleotide (phosphate) (NAD(P)), while others may use coenzymes such as flavin adenine dinucleotide (FAD) or pyrroloquinolinequinone (PQQ).

In test-sensor applications, the redox equivalents generated in the course of the oxidation of glucose are transported to the surface of an electrode, whereby an electrical signal is generated. The magnitude of the electrical signal is then correlated with glucose concentration. The transfer of redox equivalents from the site of chemical reaction in the enzyme to the surface of the electrode is accomplished using electron transfer mediators.

Many mediators such as, for example, ferricyanide have a high background current such that the signal-to-noise ratio when formulated in a glucose test sensor is low. Typically, a low signal-to-noise ratio results in a higher assay imprecision, particularly at lower glucose levels and high hematocrit sample levels. With quicker sample tests (e.g., test times less than 10 seconds), it may be difficult to burn off the high background current in the time allocated to perform the test. Because of the quicker sample test times, this necessitates that the active ingredients interact rapidly when sample is applied to give a rapid response.

Therefore, it would be desirable to form a mediator that has a low background current, while still having other desirable attributes of a mediator including stability.

SUMMARY OF THE INVENTION

A method of forming a 3-phenylimino-3H-phenothiazine mediator includes providing a first reactant including phenothiazine. A first solvent is provided in which the phenothiazine has a desired solubility therein. A second reactant is provided to assist in forming the 3-phenylimino-3H-phenothiazine mediator. A second solvent is provided in which the second reactant has a desired solubility therein. The first reactant, first solvent, second reactant and second solvent are combined to form a reactants solution. Sodium persulfate is added to the reactants solution to couple the first and second reactants resulting in a reaction solution including the 3-phenylimino-3H-phenothiazine mediator. After adding the sodium persulfate, the reaction solution is further processed to include the 3-phenylimino-3H-phenothiazine mediator so as to isolate the 3-phenylimino-3H-phenothiazine mediator.

A method of forming a 3-phenylimino-3H-phenoxazine mediator includes providing a first reactant including phenoxazine. A first solvent is provided in which the phenoxazine has a desired solubility therein. A second reactant is provided to assist in forming the 3-phenylimino-3H-phenoxazine mediator. A second solvent is provided in which the second reactant has a desired solubility therein. The first reactant, first solvent, second reactant and second solvent are combined to form a reactants solution. Sodium persulfate is added to the reactants solution to couple the first and second reactants resulting in a reaction solution including the 3-phenylimino-3H-phenoxazine mediator. After adding the sodium persulfate, the reaction solution is further processed to include the 3-phenylimino-3H-phenoxazine mediator so as to isolate the 3-phenylimino-3H-phenoxazine mediator.

A method of forming and stabilizing a 3-phenylimino-3H-phenothiazine mediator or 3-phenylimino-3H-phenoxazine mediator includes providing a first reactant including phenothiazine or phenoxazine. A first solvent is provided in which the phenothiazine or the phenoxazine has a desired solubility therein. A second reactant is provided to assist in forming the 3-phenylimino-3H-phenothiazine mediator or the 3-phenylimino-3H-phenothiazine mediator. A second solvent is provided in which the second reactant has a desired solubility therein. The first reactant, first solvent, second reactant and second solvent are combined to form a reactants solution. A coupling agent is added to the reactants solution to couple the first and second reactants resulting in a reaction solution including the 3-phenylimino-3H-phenothiazine mediator or the 3-phenylimino-3H-phenoxazine mediator. After adding the coupling agent, the reaction solution is further processed to include the 3-phenylimino-3H-phenothiazine mediator or the 3-phenylimino-3H-phenoxazine mediator so as to isolate the 3-phenylimino-3H-phenothiazine mediator or the 3-phenylimino-3H-phenoxazine mediator. The 3-phenylimino-3H-phenothiazine mediator or the 3-phenylimino-3H-phenoxazine mediator is stabilized to a pH of from about 5 to about 8.

BRIEF DESCRIPTION OF THE DRAWINGS

FIG. 1b is a side view of the test sensor of FIG. 1a.

FIG. 3b is a plot of change in background current between a baseline and the background current measured in FIG. 3a.

DETAILED DESCRIPTION OF ILLUSTRATED EMBODIMENTS

In one process, the present invention is directed to an improved method of producing a low background current 3-phenylimino-3H-phenothiazine mediator or 3-phenyliminio-3H-phenoxazine mediator. In another process, the present invention is directed to an improved method of stabilizing a low background current 3-phenylimino-3H-phenothiazine mediator or 3-phenyliminio-3H-phenoxazine mediator. The 3-phenylimino-3H-phenothiazine mediators or 3-phenyliminio-3H-phenoxazine mediators are useful mediators for electrochemical test sensors and in one example are useful in the electrochemical regeneration (oxidation) of NADH.

Mediators to be formed in the present invention include phenothiazines having the formula and phenoxazines having the formula wherein $R^1$, $R^2$, $R^3$, $R^4$, $R^5$, $R^6$, $R^7$, $R^8$, and $R^9$ are the same or different and are independently selected from the group consisting of hydrogen, alkyl, alkenyl, alkynyl, aryl, heteroaryl, cyclic, heterocyclic, halo, haloalkyl, carboxy, carboxyalkyl, alkoxycarbonyl, aryloxycarbonyl, aromatic keto, aliphatic keto, alkoxy, aryloxy, nitro, dialkylamino, aminoalkyl, sulfo, dihydroxyboron, and combinations thereof. It is contemplated that isomers of the same may also be formed.

The 3-phenylimino-3H-phenothiazine mediator or 3-phenyliminio-3H-phenoxazine mediator is adapted to be used with electrochemical test sensors. The electrochemical test sensors are adapted to receive a fluid sample and be analyzed using an instrument or meter. The test sensor assists in determining information related to the analytes such as analyte concentrations. Analytes that may be measured include glucose, cholesterol, lipid profiles, microalbumin, urea, creatinine, creatine, fructose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids.

Figure 1A:
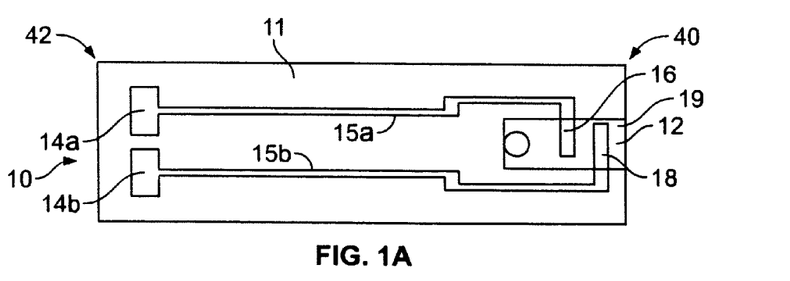
FIG. 1a is a test sensor according to one embodiment.

The test sensors described herein are electrochemical test sensors. Meters used with the electrochemical test sensors may have optical aspects so as to detect the calibration information and electrochemical aspects to determine the information related to the analyte (e.g., analyte concentration of the fluid sample). One non-limiting example of an electrochemical test sensor is shown in FIG. 1a. FIG. 1a depicts a test sensor 10 including a base 11, a capillary channel, and a plurality of electrodes 16 and 18. A region 12 shows an area that defines the capillary channel (e.g., after a lid is placed over the base 11). The plurality of electrodes includes a counter electrode 16 and a working (measuring) electrode 18. The electrochemical test sensor may also contain at least three electrodes, such as a working electrode, a counter electrode, a trigger electrode, or a hematocrit electrode. The working electrode employed in electrochemical sensors according to the embodiments of the present invention may vary, with suitable electrodes including, but not limited to, carbon, platinum, palladium, gold, ruthenium, rhodium and combinations thereof.

The electrodes 16, 18 are coupled to a plurality of conductive leads 15a,b, which, in the illustrated embodiment, terminates with larger areas designated as test-sensor contacts 14a,b. The capillary channel is generally located in a fluid-receiving area 19. It is contemplated that other electrochemical test sensors may be employed with the mediators of the present invention.

The fluid-receiving area 19 includes at least one reagent for converting the analyte of interest (e.g., glucose) in the fluid sample (e.g., blood) into a chemical species that is electrochemically measurable, in terms of the electrical current it produces, by the components of the electrode pattern. The reagent typically includes an analyte-specific enzyme that reacts with the analyte and with an electron acceptor to produce an electrochemically measurable species that may be detected by the electrodes. The reagent includes a mediator that assists in transferring electrons between the analyte and the electrodes. The reagent may include binders that hold the enzyme and mediator together, other inert ingredients, or combinations thereof.

A fluid sample (e.g., blood) may be applied to the fluid-receiving area 19. The fluid sample reacts with the at least one reagent. After reacting with the reagent and in conjunction with the plurality of electrodes, the fluid sample produces electrical signals that assist in determining the analyte concentration. The conductive leads 15a,b carry the electrical signal back toward a second opposing end 42 of the test sensor 10 where the test-sensor contacts 14a,b transfer the electrical signals into the meter.

Figure 1B:
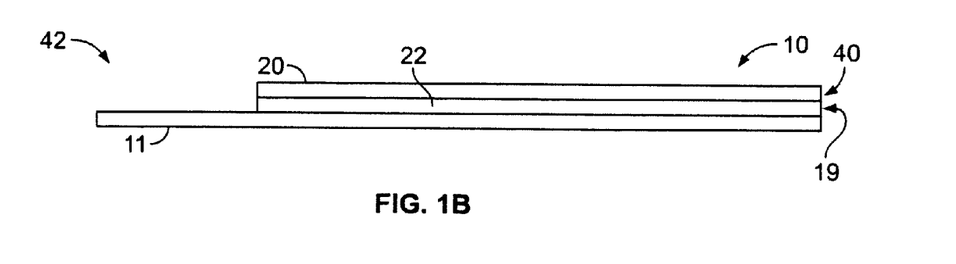

Referring to FIG. 1b, a side view of the test sensor 10 of FIG. 1a is shown. As shown in FIG. 1b, the test sensor 10 of FIG. 1b further includes a lid 20 and a spacer 22. The base 11, the lid 20, and the spacer 22 may be made from a variety of materials such as polymeric materials. Non-limiting examples of polymeric materials that may be used to form the base 11, the lid 20, and the spacer 22 include polycarbonate, polyethylene terephthalate (PET), polyethylene naphthalate (PEN), polyimide, and combinations thereof. It is contemplated that other materials may be used in forming the base 11, lid 20, and/or spacer 22.

To form the test sensor 10 of FIGS. 1a, 1b, the base 11, the spacer 22, and the lid 20 are attached by, for example, an adhesive or heat sealing. When the base 11, the lid 20, and the spacer 22 are attached, the fluid-receiving area 19 is formed.

The fluid-receiving area 19 provides a flow path for introducing the fluid sample into the test sensor 10. The fluid-receiving area 19 is formed at a first end or testing end 40 of the test sensor 10. Test sensors of the embodiments of the present invention may be formed with a base and a lid in the absence of a spacer, where the fluid-receiving area is formed directly in the base and/or the lid.

It is also contemplated that the electrochemical test sensor may be formed in the absence of a spacer. For example, the electrochemical test sensor may include a base and a lid such that a channel (e.g., capillary channel) is formed when the base and the lid are attached to each other.

The base, spacer and lid may be made from a variety of materials such as polymeric materials. Non-limiting examples of polymeric materials that may be used to form the base, spacer and lid include polycarbonate, polyethylene terephthalate (PET), polystyrene, polyimide, and combinations thereof. It is contemplated that the base, spacer and lid may be independently made of other materials. The electrode pattern may be made from a variety of conductive materials including, but not limited to, gold, platinum, rhodium, palladium, ruthenium, carbon or combinations thereof.

In another embodiment, the 3-phenylimino-3H-phenothiazine mediator or 3-phenyliminio-3H-phenoxazine mediator may be used in an optical test sensor. The 3-phenylimino-3H-phenothiazine mediator or 3-phenyliminio-3H-phenoxazine mediator would be a stable mediator in such a system.

In one method, a 3-phenylimino-3H-phenothiazine mediator is formed and includes providing a first reactant including phenothiazine. A first solvent is provided in which the phenothiazine has a desired solubility therein. A second reactant is provided to assist in forming the 3-phenylimino-3H-phenothiazine mediator. A second solvent is provided in which the second reactant has a desired solubility therein. The first reactant and the first solvent are combined together to form a first reactant solution. The second reactant and second solvent are combined together to form a second reactant solution. The first and second reactant solutions are combined together to form a reactants solution. A solution of sodium persulfate is prepared and added to the reactants solution. The solution of sodium persulfate is typically formed using the second solvent (same solvent as used in forming the second reactant solution). The sodium persulfate causes coupling of the first and second reactants resulting in a reaction solution with formed product.

In this method, further processing occurs to the reaction solution so as to isolate a 3-phenylimino-3H-phenothiazine mediator. In one embodiment, the 3-phenylimino-3H-phenothiazine mediator is in the form of a salt. In another embodiment, the 3-phenylimino-3H-phenothiazine mediator is in the form of an acid. Some 3-phenylimino-3H-phenothiazine mediators may not be in the form of the salt or acid.

A second reactant is selected to form the desired 3-phenylimino-3H-phenothiazine mediator. For example, the second reagent may be aniline 2,5-disulfonic acid. When aniline 2,5-disulfonic acid is used, the specific 3-phenylimino-3H-phenothiazine mediator formed is (3-(2',5'-disulfophenylimino)-3H-phenothiazine mediator.

It is contemplated that other second reactant may be used to form different 3-phenylimino-3H-phenothiazine mediators. For example, the second reactant for forming a 3-phenylimino-3H-phenothiazine mediator may be selected from the following: 4-diethylaminoaniline; 4-chloroaniline; 4-ethylaniline; 4-trifluoromethylaniline; methyl 4-aminobenzoate; 4-nitroaniline; 4-methoxyaniline; 4-(4'-aminophenyl)butyric acid; 4-aminobenzyl amine; 4-(2'-aminoethyl)aniline; 5-amino-1,3-benzenedicarboxylic acid; 4-aminobenzoic acid; 2,5-(4'-aminophenyl)-1,3,4-oxadiazole; 4-[2'-(2'-ethanoloxy)ethoxy]ethoxyaniline; and 2,5-disulfoaniline. It is contemplated that other second reactants may be used to form other 3-phenylimino-3H-phenothiazine mediators.

A first solvent is selected that is compatible with the first reactant. It is desirable for the first reactant to have a generally high solubility into the first solvent. In one method, the first solvent is tetrahydrofuran (THF). The first solvent is desirably tetrahydrofuran (THF) because the phenothiazine has a generally high solubility therein. The first solvent is also desirably miscible with the second solvent so as to form a generally or substantially uniform solution.

It is contemplated that other first solvents may be used instead of tetrahydrofuran (THF) such as, for example, N,N-dimethylformamide, methanol, ethanol, 1,4-dioxane and sulfolane. It is also contemplated that other first solvents may be used.

A second solvent is selected that is compatible with the second reactant. It is desirable for the second reactant to have a generally high solubility into the second solvent. In one method, the second solvent is water. In another method, the second solvent is a combination of water and sodium hydroxide (NaOH). The sodium hydroxide is desirable because the solubility of at least some second reactants are improved by being more basic. It is contemplated that other basic solutions may be added with the second solvent to achieve improved solubility of the second reactant therein. It is contemplated that other second solvents may be used instead of water.

Sodium persulfate promotes coupling between the first and second reactants. Sodium persulfate is a desirable coupling agent because it is believed to avoid forming undesirable by-products. Using sodium persulfate as the coupling agent assists in obtaining a consistent low background current, which means a generally low amount of undesirable by-products are being formed and remaining in the solution. Additionally, the use of sodium persulfate assists in easier isolation of the desired 3-phenylimino-3H-phenothiazine mediator from the reaction by facilitating precipitation of organic material.

To form the 3-phenylimino-3H-phenothiazine mediator, further processing occurs after the coupling agent is added to the reactants solution including the first reactant, first solvent, second reactant and the second solvent. The first solvent (e.g., tetrahydrofuran) may be removed or extracted from the solution. The first solvent may be removed by, for example, ethyl acetate. Ethyl acetate assists in extracting the first solvent and also may assist in removing other undesirable residual organic material (e.g., water-soluble organic materials) from the reaction solution.

It is contemplated that other compounds may be used to remove the first solvent such as, for example, diethyl ether, chloroform and dichloromethane.

The second solvent (e.g., water) is removed from the product by cooling and filtration. By removing the second solvent, this also aids in preventing or inhibiting decomposition. By preventing or inhibiting decomposition, the background current will typically be at a more desired lower level. Residual second solvent (e.g., residual water) not removed by, for example, cooling and filtration may be removed from the product by several methods. For example, the residual second solvent may be removed by (a) drying in a vacuum oven, (b) adding a compound to the product, or (c) lypholization of a solution of the product.

In one process, acetonitrile is added to the residual second solvent to assist in removing the residual second solvent from the solution. It is contemplated that other compounds may be used to remove the residual second solvent such as, for example, acetone and toluene.

It is contemplated that other processing may occur in forming the 3-phenylimino-3H-phenothiazine mediator. For example, a processing act before the removal of the second solvent may include reconstituting the mediator in water, cooling and then filtering at room temperature to remove some of the excess salts. It is also contemplated that other processing acts may occur.

In another method, a 3-phenylimino-3H-phenoxazine mediator is formed and includes providing a first reactant including phenoxazine. A first solvent is provided in which the phenoxazine has a desired solubility therein. A second reactant is provided to assist in forming the 3-phenylimino-3H-phenoxazine mediator. A second solvent is provided in which the second reactant has a desired solubility therein. The first reactant and the first solvent are combined together to form a first reactant solution. The second reactant and second solvent are combined together to form a second reactant solution. The first and second reactant solutions are combined together to form a reactants solution. A solution of sodium persulfate is prepared and added to the reactants solution. The solution of sodium persulfate is typically formed using the second solvent (same solvent as used in forming the second reactant solution). The sodium persulfate causes coupling of the first and second reactants resulting in a reaction solution with formed product.

In this method, further processing occurs to the reaction solution so as to isolate a 3-phenylimino-3H-phenoxazine mediator. In one embodiment, the 3-phenylimino-3H-phenoxazine mediator is in the form of a salt. In another embodiment, the 3-phenylimino-3H-phenoxazine mediator is in the form of an acid. Some 3-phenylimino-3H-phenoxazine mediators may not be in the form of a salt or acid.

In this method if forming the 3-phenylimino-3H-phenoxazine mediator, the same or similar second reactants, first solvents, second solvents may be used as described above with respect to the method of forming the 3-phenylimino-3H-phenothiazine mediator. Additionally, the processing of isolating the 3-phenylimino-3H-phenoxazine mediator by substantially removing at least the first and second solvent may be performed in a similar or the same manner as described above with respect to 3-phenylimino-3H-phenothiazine mediator.

It is contemplated that many different 3-phenylimino-3H-phenothiazine mediators or 3-phenyliminio-3H-phenoxazine mediators may be formed using the inventive processes. One desirable example of a phenothiazine that has been prepared and found to have suitable properties as an NADH mediator is 3-(2',5' disulfophenylimino)-3H-phenothiazine mediator. Another desirable example is 3-(3',5'-dicarboxy-phenylimino)-3H-phenothiazine mediator that has been prepared and found to have suitable properties as an NADH mediator.

Among those phenothiazines and phenoxazines that have been prepared and found to have suitable properties as NADH mediators are 3-(4'-chloro-phenylimino)-3H-phenothiazine; 3-(4'-diethylamino-phenylimino)-3H-phenothiazine; 3-(4'-ethyl-phenylimino)-3H-phenothiazine; 3-(4'-trifluoromethyl-phenylimino)-3H-phenothiazine; 3-(4'-methoxycarbonyl-phenylimino)-3H-phenothiazine; 3-(4'-nitro-phenylimino-3H-phenothiazine; 3-(4'-methoxy-phenylimino)-3H-phenothiazine; 7-acetyl-3-(4'-methoxycarbonylphenylimino)-3H-phenothiazine; 7-trifluoromethyl-3-(4'-methoxycarbonyl-phenylimino)-3H-phenothiazine; 3-(4'-ω-carboxy-n-butyl-phenylimino)-3H-phenothiazine; 3-(4'-aminomethyl-phenylimino)-3H-phenothiazine; 3-(4'-(2"-(5"-(p-aminophenyl)-1,3,4-oxadiazoyl)phenylimino)-3H-phenothiazine; 3-(4'-β-aminoethyl-phenylimino)-3H-phenothiazine; 6-(4'-ethylphenyl)amino-3-(4'-ethylphenylimino)-3H-phenothiazine; 6-(4'-[2-(2-ethanoloxy)ethoxy]-ethoxyphenyl)amino-3-(4'-[2-(2-ethanoloxy)ethoxy]ethoxyphenylimino)-3H-phenothiazine; 3-(4'-[2-(2-ethanoloxy)ethoxy]ethoxy-phenylimino)-3H-phenothiazine; 3-(4'-phenylimino)-3H-phenothiazineboronic acid, 3-(3',5'-dicarboxy-phenylimino)-3H-phenothiazine; 3-(4'-carboxyphenylimino)-3H-phenothiazine; 3-(3',5-dicarboxy-phenylimino)-3H-phenoxazine; 3-(2',5'-phenylimino)-3H-phenothiazinedisulfonic acid; and 3-(3'-phenylimino)-3H-phenothiazinesulfonic acid.

It is contemplated that the phenothiazines and phenoxazines that have been prepared and found to have suitable properties may be used with flavoproteins such as FAD-glucose oxidase, flavin-hexose oxidase and FAD-glucose dehydrogenase. It is also contemplated that the phenothiazines and phenoxazines may be prepared to be used and have suitable properties with quionoproteins such as, for example, PQQ-glucose dehydrogenase.

In another process, the stabilization of 3-phenylimino-3H-phenothiazine mediator or 3-phenylimino-3H-phenoxazine mediator may also be improved by neutralization or buffering. The neutralization of buffering act assists in stabilizing the mediator so that it is robust during storage conditions that are encountered. It is contemplated that the neutralization or buffering act may occur before or after further processing has occurred to isolate the mediator. For example, the neutralization or buffering act may occur before the mediator is dried to a powder form. In another example, the neutralization or buffering act may occur after the mediator has been dried to a powder form.

The neutralizing or buffering agent may be selected from materials including, but not limited to, sodium hydroxide, sodium bicarbonate, sodium phosphate, tetrabutylammonium hydroxide, calcium hydroxide, potassium hydroxide, potassium phosphate, potassium bicarbonate and combinations thereof. It is contemplated that other materials may be used as the neutralizing or buffering agent.

After the neutralizing or buffering agent is added to the mediator solution, the pH is generally from about 5 to about 8. More typically, after the neutralizing or buffering agent is added to the mediator solution, the pH is from about 5.5 to about 7 and, even more desirably from about 6 to about 7.

EXAMPLES

Example 1

Preparation of (3-(2',5'-Disulfophenylimino)-3H-Phenothiazine Mediator

Phenothiazine (1.53 mole, 1.1 equivalent, 306 g) was dissolved with stirring into 6.0 L of tetrahydrofuran (THF) and then cooled to 0° C. Aniline 2,5-disulfonic acid (1.38 mole, 350 g) was dissolved in 7.0 L of water and 1 M sodium hydroxide (NaOH) (128 ml) was added during stirring. The aniline 2,5-disulfonic acid solution was added slowly, over the course of about 2 hrs, to the phenothiazine solution, to give a white, cloudy suspension. The phenothiazine/aniline suspension was at a temperature of about 0° C.-4° C. Sodium persulfate (5.52 mole, 4 equivalent, 1314 g) was dissolved in 4.0 L of water to form a sodium persulfate solution.

The sodium persulfate solution was added dropwise over 3 hours to the phenothiazine/aniline suspension at a temperature between about 0° C.-3° C. and resulted in a very dark solution. The very dark solution remained cold using an ice bath and was stirred overnight. The contents were then transferred to a Buchi rotary evaporator and the tetrahydrofuran was removed over the course of about 2 hours at a temperature less than 35° C. After the evaporation act, the remaining solution was transferred to a 25 L separator and backwashed with ethyl acetate. The remaining solution was backwashed 3 times using 2 L of ethyl acetate each time. The reaction fluids were cooled while stirring to −3° C. in an acetone/$CO_2$ bath. The precipitated solid was filtered through two cloths on two 24 cm Buchner funnels on the same day. The precipitated solid was left overnight in the funnels to dry and then transferred to a flask containing 2 L of acetonitrile and stirred for about 1 hour at room temperature. To remove the residual water, the sample was then filtered and washed with more acetonitrile. The mediator was dried to a constant weight in a vacuum oven at 35° C. The mediator formed using this process was 3-(2',5'-phenylimino)-3H-phenathiazinedisulfonic acid or 3-(2',5'-disulfophenylimino)-3H-phenothiazine. The mediator is shown as follows:

Example 2

Background Current of Inventive and Comparative Processes

The background currents of 3-(2',5'-disulfophenylimino)-3H-phenothiazine mediators prepared by two different processes were compared. The Inventive process for forming the 3-(2',5'-disulfophenylimino)-3H-phenothiazine mediator used sodium persulfate as the coupling agent and was substantially the same as the process described above in Example 1. This mediator will be referred to as the Inventive mediator. The Comparative process for forming the 3-(2',5'-disulfophenylimino)-3H-phenothiazine mediator used ammonium persulfate as the coupling agent. The Comparative process was the substantially the same as the Inventive process except for the use of sodium persulfate as the coupling agent. This mediator will be referred to as the Comparative mediator.

Each of the Inventive and Comparative mediators were separately added to a buffered solution. Each of the buffered solutions included 100 mM of sodium phosphate. After the Inventive and Comparative mediators were added to the buffered solutions, a pH in both solutions was adjusted to 7.2. The Inventive and Comparative mediator solutions were then individually placed on carbon electrodes. After three seconds, a potential of 250 mV was then applied for five seconds to the carbon electrodes and then readings of the respective mediator background currents were taken.

Figure 2:
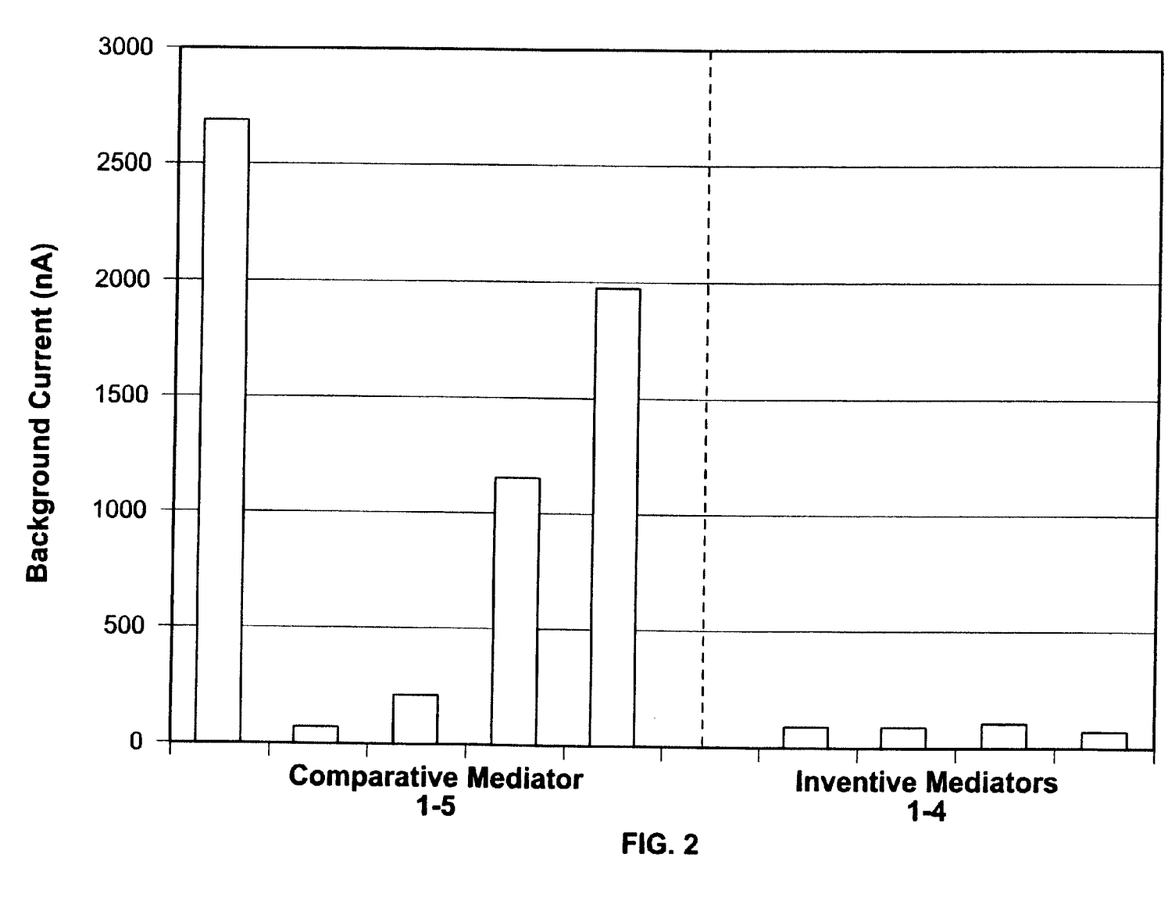
FIG. 2 is a plot of background current versus various lots of inventive and comparative mediators.

Referring to FIG. 2, background currents (in nA) of the 3-(2',5'-disulfophenylimino)-3H-phenothiazine mediators were plotted for different lots of mediators formed by the Inventive and Comparative processes. Specifically, five different Comparative mediators (referred to as Comparative mediators 1-5) and four different Inventive mediators (referred to as Inventive mediators 1-4) were tested from different lots.

As shown in FIG. 2, there were three lots of Comparative mediators that had very high background currents. See Comparative mediators 1, 4 and 5 of FIG. 2 having respective background currents of 2687, 1158 and 1971 nA. Comparative mediator 2 had a background current of 75 nA, while Comparative mediator 3 had a background current of 221 nA. All of the Inventive mediators 1-4 had a desirable background current of less than about 100 nA. Specifically, Inventive mediators 1-4 had respective background currents of 88, 93, 106 and 99 nA.

Example 3

Comparison of Stabilities of 3-(2',5'-Disulfophenylimino)-3H-Phenothiazine Using Different Processes The stabilities of 3-(2',5'-disulfophenylimino)-3H-phenothiazine prepared by two different process were compared. The Inventive process for forming the 3-(2',5'-disulfophenylimino)-3H-phenothiazine mediator used sodium persulfate as the coupling agent and was substantially the same as the process described above in Example 1. This mediator will be referred to as the Inventive mediator. The Comparative process for forming the 3-(2',5'-disulfophenylimino)-3H-phenothiazine mediator used ammonium persulfate as the coupling agent. The Comparative process was substantially the same as the Inventive process except for the use of sodium persulfate as the coupling agent. This mediator will be referred to as the Comparative mediator.

The stabilities of the Inventive and Comparative mediators were compared. Mediators from both the Inventive and Comparative processes were formulated into respective reagent mixtures. The reagent mixtures further included phosphate buffer, Fad-GDH, cellulose polymer and surfactant. The reagent mixtures were placed onto gold electrodes to form a glucose test sensor. The test sensor samples with Inventive and Comparative mediators were exposed to a temperature of −20° C. for a duration of two weeks. Test sensors formulated with mediators from the same lot of the Inventive and Comparative processes were also exposed to a temperature of 50° C. for a duration of two weeks.

The reagent mixtures included the exposed Inventive mediator or Comparative mediator. The response of the electrodes were measured at 250 mV applied potential using four different concentrations (0 mg/dl, 50 mg/dl, 100 mg/dl and 400 mg/dl) of whole blood glucose samples with a Yellow Springs Glucose Analyzer (YSI, Inc., Yellow Springs, Ohio). The electrical responses were converted into glucose concentrations using the slope and intercept of the respective reagents as referenced to the YSI glucose measurements. The glucose concentrations were tested and compared for the reagents including the Inventive or Comparative mediator exposed between the temperatures of −20° C. and 50° C. and compared to see if there was any variance or bias therebetween. For example, using 50 mg/dL of glucose, the reagent including the Inventive mediator was compared between the temperatures of −20° C. and 50° C. to see if there was any variance between the readings. The % bias between these readings was determined.

The % bias is shown for each of the different glucose concentrations and the Inventive and Comparative mediators are in Table 1 as follows:

TABLE 1

| | Inventive Process | Comparative Process |
|---|---|---|
| 0 mg/dL | −0.7% | 7.1% |
| 50 mg/dl | −1.8% | 5.9% |
| 100 mg/dl | 0.2% | 4.9% |
| 400 mg/dl | 2.4% | −8.2% |

Thus, as shown in Table 1, the 3-(2',5'-disulfophenylimino)-3H-phenothiazine formed using the Inventive process had much greater stability after being exposed to 50° C. for two weeks than the 3-(2',5'-disulfophenylimino)-3H-phenothiazine formed using the Comparative Process. The Inventive process had greater stability because the measured glucose concentrations did not vary much after exposure to the temperature of 50° C. as shown by the low % biases. The Comparative process, on the other hand, had much less stability because the measured glucose concentrations varied much more than the Inventive Process after exposure to the temperature of 50° C. as shown by the higher % biases.

Example 4

Effect of Neutralization or Buffering on 3-(2',5'-Disulfophenylimino)-3H-Phenothiazine with Respect to Stability In each of the neutralization or buffering tests of Example 4, the same 3-(2',5'-disulfophenylimino)-3H-phenothiazine mediator was used. The same mediator was also used in the tests that did not include a neutralization or buffering test. The 3-(2',5'-disulfophenylimino)-3H-phenothiazine mediator was formed using sodium persulfate as the coupling agent and was substantially the same as the process described above in Example 1.

Figure 3A:
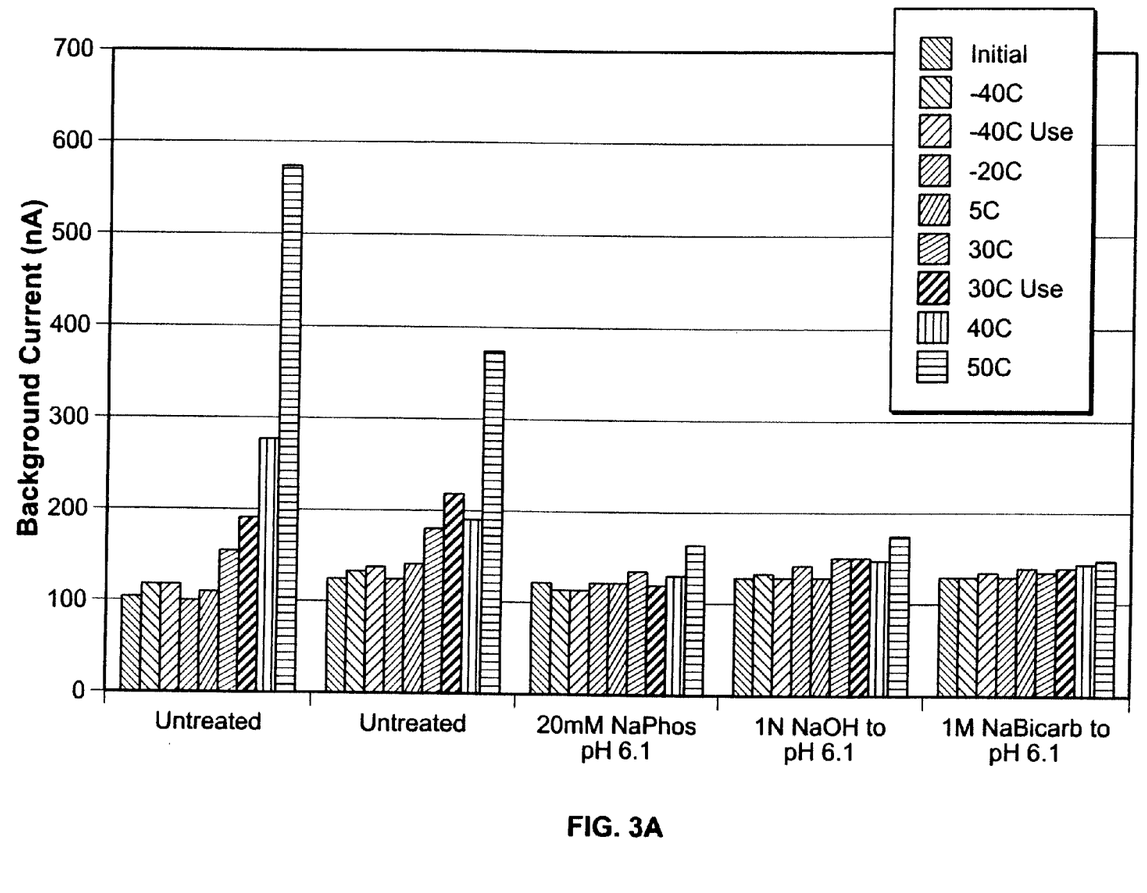
FIG. 3a is a plot of background current using several neutralization or buffering processes and some processes without neutralization or buffering.
Figure 3B:
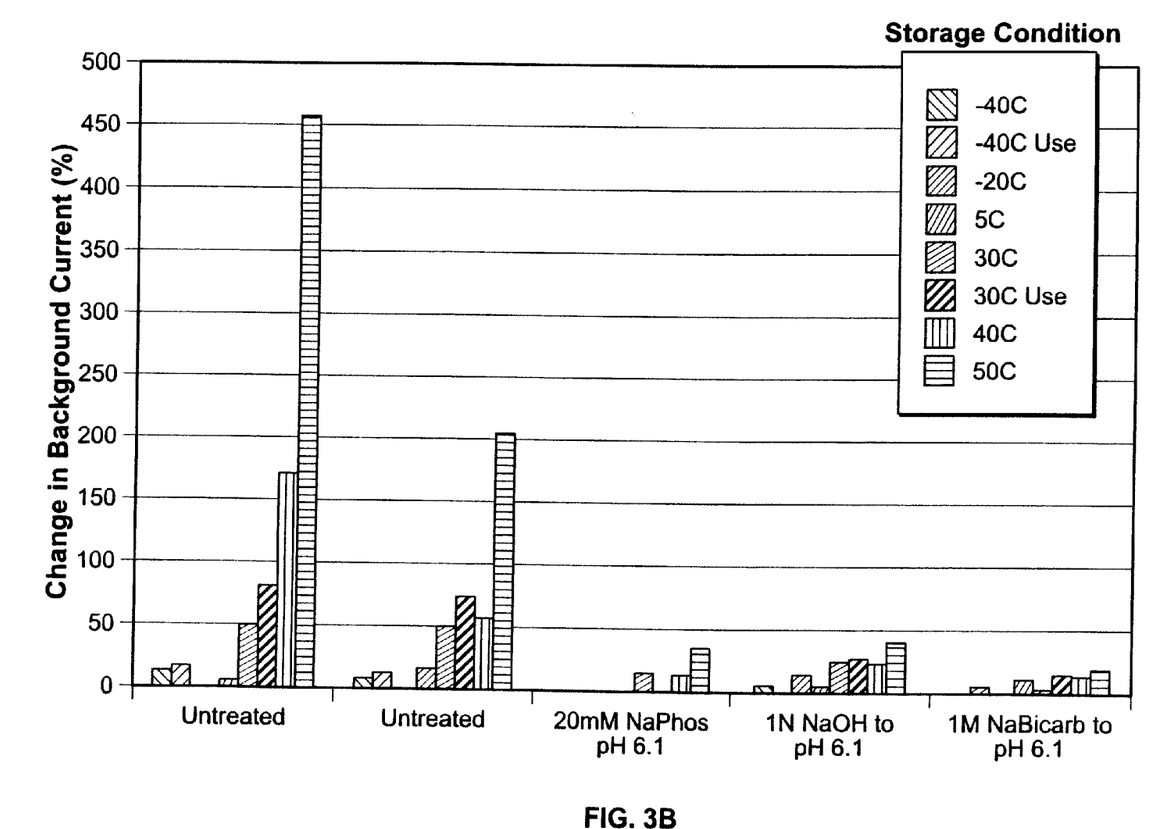

Example 4 tested three processes using different neutralization or buffering agents and compared these to two processes that did not include a neutralizing or buffering agent. Referring to FIGS. 3a,3b, the processes for forming Mediators 1 and 2 did not include any neutralization or buffering acts. The process for forming Mediator 1 included drying the mediator by a vacuum oven. The process for forming Mediator 2 included lyophilizing that was controlled at a pH of 2.4.

Each of the processes of forming Mediators 3-5 included a neutralization or buffering act. Each of the neutralizing or buffering acts resulted in a pH of 6.1. Specifically, Mediator 3 used 20 mM of sodium phosphate. This solution was formed by taking 5 grams of 3-(2',5'-disulfophenylimino)-3H-phenothiazine mediator and dissolving the same into 20 mM sodium phosphate buffer having a pH of 7.2. The pH was adjusted to 6.1 with 1M NaOH. The use of sodium phosphate buffer is generally referred to as a pH adjustment.

Mediator 4 used 1M of sodium hydroxide. This solution was formed by taking 5 grams of 3-(2',5'-disulfophenylimino)-3H-phenothiazine and dissolving the same into 100 mL of cold water. 1M sodium hydroxide solution was added dropwise while stirring until a measured pH of 6.1 was obtained. The use of sodium hydroxide in this method neutralizes the solution and, thus, would be referred to as a neutralizing agent.

Mediator 5 used 1M of sodium bicarbonate. This solution was formed by taking 5 grams of 3-(2',5'-disulfophenylimino)-3H-phenothiazine and dissolving the same into 100 mL of cold water. 1M sodium bicarbonate solution was added dropwise while stirring until a measured pH of 6.1 was obtained. The use of sodium bicarbonate in this method neutralizes the solution and, thus, would be referred to as a neutralizing agent.

Each of the Mediators 3-5 were then froze in an isopropanol/dry ice bath and lyophilized to a dry powder using a VirTis® Model No. 4 KBTXL benchtop 4K Freeze Dryer model (Gardiner, N.Y.).

The dried powder form of the Mediators 1-5 was stressed for two weeks under various storage conditions. Specifically, nine different conditions were tested in which the temperatures ranged from −40° C. to 50° C. Before being exposed to the temperature conditions, the dried samples were placed into glass vials, sealed with caps and then stored. Two tests were performed at −40° C. and 30° C. in which a "use" component was added. Specifically, the "use" component included exposing Mediators 1-5 to ambient temperature for a period of 30 minutes before sealing the cap and opening the cap after one week and re-exposing to ambient temperature for another period of 30 minutes. This "use" exposure was done only at respective temperatures −40° C. and 30° C. The "initial" testing performed the testing with no storage conditions.

Each of the mediator samples was tested for background current using a background current screening assay. The mediator samples were prepared as in Example 1 and with a pH adjustment to 7.2 using 100 mM sodium phosphate as described in Example 2. These mediator samples were added to a carbon electrode. After three seconds, a 250 mV potential was applied for a period of five seconds and then the background current was measured.

As shown in FIG. 3a, the background current (in nA) was much lower in the mediators that included the neutralization or buffering act when exposed to higher temperatures during this time period. Compare background currents at temperatures greater than 25° C. for Mediators 1-5. This was especially the case at the highest exposure temperature of 50° C.

FIG. 3b depicts the change in the background current (%) between the measured background current of FIG. 3a from the baseline that was measured before the different exposures. Similarly, the background current (%) was much lower in the mediators that included the neutralization or buffering act when exposed to higher temperatures during this time period. Compare % change in background currents at temperatures greater than 25° C. for Mediators 1-5. This was especially the case at the highest exposure temperature of 50° C.

Process A

A method of forming a 3-phenylimino-3H-phenothiazine mediator, the method comprising the acts of:

providing a first reactant including phenothiazine;

providing a first solvent in which the phenothiazine has a desired solubility therein;

providing a second reactant to assist in forming the 3-phenylimino-3H-phenothiazine mediator;

providing a second solvent in which the second reactant has a desired solubility therein;

combining the first reactant, first solvent, second reactant and second solvent to form a reactants solution;

adding sodium persulfate to the reactants solution to couple the first and second reactants resulting in a reaction solution including the 3-phenylimino-3H-phenothiazine mediator; and after adding the sodium persulfate, further processing to the reaction solution including the 3-phenylimino-3H-phenothiazine mediator so as to isolate the 3-phenylimino-3H-phenothiazine mediator.

Process B
The method of alternative process A wherein the first solvent includes tetrahydrofuran (THF).
Process C
The method of alternative process A wherein the second solvent includes water.
Process D
The method of alternative process C wherein the second solvent further includes sodium hydroxide.
Process E
The method of alternative process A wherein combining the first reactant, first solvent, second reactant and second solvent including the acts of combining the first reactant and the first solvent to form a first reactant solution, and combining the second reactant and the second solvent to form a second reactant solution before the first reactant, first solvent, second reactant and second solvent are combined together to form the reactants solution.
Process F
The method of alternative process A wherein further processing includes generally removing the second solvent by adding acetonitrile.
Process G
The method of alternative process A wherein further processing includes generally removing the first solvent by adding ethyl acetate.
Process H
The method of alternative process A wherein the second reactant includes aniline 2,5-disulfonic acid.
Process I
The method of alternative process A wherein the further processing includes substantially removing at least the first solvent and second solvent from the second solution so as to isolate the 3-phenylimino-3H-phenothiazine mediator.
Process J
The method of alternative process A wherein the 3-phenylimino-3H-phenothiazine mediator is in the form of a salt.
Process K
The method of alternative process A wherein the 3-phenylimino-3H-phenothiazine mediator is in the form of an acid.
Process L
A method of forming a 3-phenylimino-3H-phenoxazine mediator, the method comprising the acts of:
providing a first reactant including phenoxazine;
providing a first solvent in which the phenoxazine has a desired solubility therein;
providing a second reactant to assist in forming the 3-phenylimino-3H-phenoxazine mediator;
providing a second solvent in which the second reactant has a desired solubility therein;
combining the first reactant, first solvent, second reactant and second solvent to form a reactants solution;
adding sodium persulfate to the reactants solution to couple the first and second reactants resulting in a reaction solution including the 3-phenylimino-3H-phenoxazine mediator; and
after adding the sodium persulfate, further processing to the reaction solution including the 3-phenylimino-3H-phenoxazine mediator so as to isolate the 3-phenylimino-3H-phenoxazine mediator.
Process M
The method of alternative process L wherein the first solvent includes tetrahydrofuran (THF).
Process N
The method of alternative process L wherein the second solvent includes water.

Process O
The method of alternative process N wherein the second solvent further includes sodium hydroxide.
Process P
The method of alternative process L wherein combining the first reactant, first solvent, second reactant and second solvent including the acts of combining the first reactant and the first solvent to form a first reactant solution, and combining the second reactant and the second solvent to form a second reactant solution before the first reactant, first solvent, second reactant and second solvent are combined together to form the reactants solution.
Process Q
The method of alternative process L wherein further processing includes generally removing residual second solvent by adding acetonitrile.
Process R
The method of alternative process L wherein further processing includes generally removing the first solvent by adding ethyl acetate.
Process S
The method of alternative process L wherein the further processing includes substantially removing at least the first solvent and second solvent from the second solution so as to isolate the 3-phenylimino-3H-phenoxazine mediator.
Process T
The method of alternative process L wherein the 3-phenylimino-3H-phenoxazine mediator is in the form of a salt.
Process U
The method of alternative process L wherein the 3-phenylimino-3H-phenoxazine mediator is in the form of an acid.
Process V
A method of forming and stabilizing a 3-phenylimino-3H-phenothiazine mediator or 3-phenylimino-3H-phenoxazine mediator, the method comprising the acts of:
providing a first reactant including phenothiazine or phenoxazine;
providing a first solvent in which the phenothiazine or the phenoxazine has a desired solubility therein;
providing a second reactant to assist in forming the 3-phenylimino-3H-phenothiazine mediator or the 3-phenylimino-3H-phenothiazine mediator;
providing a second solvent in which the second reactant has a desired solubility therein;
combining the first reactant, first solvent, second reactant and second solvent to form a reactants solution;
adding a coupling agent to the reactants solution to couple the first and second reactants resulting in a reaction solution including the 3-phenylimino-3H-phenothiazine mediator or the 3-phenylimino-3H-phenoxazine mediator; and
after adding the coupling agent, further processing to the reaction solution including the 3-phenylimino-3H-phenothiazine mediator or the 3-phenylimino-3H-phenoxazine mediator so as to isolate the 3-phenylimino-3H-phenothiazine mediator or the 3-phenylimino-3H-phenoxazine mediator; and
stabilizing the 3-phenylimino-3H-phenothiazine mediator or the 3-phenylimino-3H-phenoxazine mediator to a pH of from about 5 to about 8.
Process W
The method of alternative process V wherein the pH is from about 5.5 to about 7.
Process X
The method of alternative process W wherein the pH is from about 6 to about 7.

Process Y

The method of alternative process W wherein the stabilizing the 3-phenylimino-3H-phenothiazine mediator or the 3-phenylimino-3H-phenoxazine mediator includes adding sodium hydroxide, sodium bicarbonate, sodium phosphate, tetrabutylammonium hydroxide, calcium hydroxide, potassium hydroxide, potassium phosphate, potassium bicarbonate or combinations thereof.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention.

What is claimed is:

1. A test sensor including a base, the base including an enzyme adapted to react with an analyte, and a mediator, the mediator having a background current being less than 200 nA after being exposed to a temperature of 50° C. for a duration of two weeks and further including a neutralizing agent, the neutralizing agent being present in an amount to obtain a pH in a range below 7 to about 5.5 in a mediator solution.

2. The test sensor of claim 1 wherein the neutralizing agent is sodium hydroxide.

3. The test sensor of claim 1 wherein the neutralizing agent is sodium bicarbonate.

4. The test sensor of claim 1 further including a buffer.

5. The test sensor of claim 4 wherein the buffer is sodium phosphate.

6. The test sensor of claim 1 wherein the test sensor is an electrochemical test sensor.

7. The test sensor of claim 1 wherein the test sensor is an optical test sensor.

8. The test sensor of claim 1 wherein the mediator is a 3-phenylimino-3H-phenothiazine mediator.

9. The test sensor of claim 1 wherein the neutralizing agent is sodium phosphate.

10. The test sensor of claim 1 wherein the neutralizing agent is present in an amount to obtain a pH in a range below 7 to about 6 in the mediator solution.

11. The test sensor of claim 1 wherein the neutralizing agent is present in an amount to obtain a pH of from about 5.5 to about 6 in the mediator solution.

12. A test sensor including a reagent, the reagent including a mediator and a neutralizing agent, the reagent having a % bias being within 2.4% between 0 and 400 mg/dL of glucose after being exposed to a temperature of 50° C. for a duration of two weeks, the neutralizing agent being present in an amount to obtain a pH in a range below 7 to about 5.5 in a mediator solution.

13. The test sensor of claim 12 wherein the reagent includes a 3-phenylimino-3H-phenothiazine mediator.

14. The test sensor of claim 12 wherein the reagent further comprises glucose dehydrogenase (GDH) and a cellulose polymer.

15. The test sensor of claim 12 wherein the test sensor includes electrodes.

16. The test sensor of claim 12 wherein the % bias is within 1.8% between 0 and 100 mg/dL of glucose after being exposed to a temperature of 50° C. for a duration of two weeks.

17. The test sensor of claim 12 wherein the neutralizing agent is present in an amount to obtain a pH in a range below 7 to about 6 in the mediator solution.

18. The test sensor of claim 12 wherein the neutralizing agent is present in an amount to obtain a pH of from about 5.5 to about 6 in the mediator solution.

19. A test sensor including electrodes and a reagent including glucose dehydrogenase (GDH), a mediator and a neutralizing agent, the reagent having a % bias being within 2.4% between 0 and 400 mg/dL of glucose after being exposed to a temperature of 50° C. for a duration of two weeks, the neutralizing agent being present in an amount to obtain a pH in a range below 7 to about 5.5 in a mediator solution.

20. The test sensor of claim 19 wherein the reagent further includes 3-phenylimino-3H-phenothiazine mediator and a cellulose polymer.

21. The test sensor of claim 19 wherein the % bias is within 1.8% between 0 and 100 mg/dL of glucose after being exposed to a temperature of 50° C. for a duration of two weeks.

22. The test sensor of claim 19 wherein the neutralizing agent is present in an amount to obtain a pH of from about 6 to about 7 in the mediator solution.

23. The test sensor of claim 19 wherein the neutralizing agent is present in an amount to obtain a pH of from about 5.5 to about 6 in the mediator solution.

24. A test sensor including a base, the base including an enzyme adapted to react with an analyte, and a 3-phenylimino-3H-phenothiazine mediator, the 3-phenylimino-3H-phenothiazine mediator having a background current being less than 200 nA after being exposed to a temperature of 50° C. for a duration of two weeks and further including a neutralizing agent, the neutralizing agent being present in an amount to obtain a pH in a range below 7 to about 6 in a mediator solution.

25. The test sensor of claim 24 wherein the neutralizing agent is present in an amount to obtain a pH of from about 5.5 to about 6 in the mediator solution.

26. The test sensor of claim 24 wherein the neutralizing agent is sodium hydroxide.

27. The test sensor of claim 24 wherein the neutralizing agent is sodium bicarbonate.

28. The test sensor of claim 24 wherein the neutralizing agent is sodium phosphate.

29. The test sensor of claim 24 further including a buffer.

30. The test sensor of claim 29 wherein the buffer is sodium phosphate.

31. The test sensor of claim 24 wherein the test sensor is an electrochemical test sensor.

32. The test sensor of claim 24 wherein the test sensor is an optical test sensor.

33. A test sensor including a base, the base including an enzyme adapted to react with an analyte, and a 3-phenylimino-3H-phenothiazine mediator, the 3-phenylimino-3H-phenothiazine mediator having a background current being less than 200 nA after being exposed to a temperature of 50° C. for a duration of two weeks and further including a neutralizing agent, the neutralizing agent being present in an amount to obtain a pH of about 6.1 in a mediator solution.

34. The test sensor of claim 33 wherein the neutralizing agent is sodium hydroxide.

35. The test sensor of claim 33 wherein the neutralizing agent is sodium bicarbonate.

36. The test sensor of claim 33 wherein the neutralizing agent is sodium phosphate.

37. The test sensor of claim 33 further including a buffer.

38. The test sensor of claim 37 wherein the buffer is sodium phosphate.

39. The test sensor of claim 33 wherein the test sensor is an electrochemical test sensor.

40. The test sensor of claim 33 wherein the test sensor is an optical test sensor.

\* \* \* \* \*